US008563253B2

(12) United States Patent
Walk et al.

(10) Patent No.: US 8,563,253 B2
(45) Date of Patent: Oct. 22, 2013

(54) MEANS AND METHOD FOR DIAGNOSING HEMOLYTIC ANEMIA

(75) Inventors: Tilmann B. Walk, Kleinmachnow (DE); Ralf Looser, Berlin (DE); Michael Manfred Herold, Berlin (DE); Jan C. Wiemer, Berlin (DE); Alexandre Prokoudine, Berlin (DE); Edgar Leibold, Berlin (DE); Bennard van Ravenzwaay, Altrip (DE); Werner Mellert, Haβloch (DE); Georgia Coelho Palermo Cunha, Sao Paulo (BR); Eric Fabian, Ludwigshafen (DE); Volker Strauss, Bad Dürkheim (DE)

(73) Assignee: Metanomics GmbH, Berlin (DE)

( * ) Notice: Subject to any disclaimer, the term of this patent is extended or adjusted under 35 U.S.C. 154(b) by 516 days.

(21) Appl. No.: 12/439,279

(22) PCT Filed: Jun. 4, 2007

(86) PCT No.: PCT/EP2007/055472
§ 371 (c)(1),
(2), (4) Date: Feb. 27, 2009

(87) PCT Pub. No.: WO2008/025579
PCT Pub. Date: Mar. 6, 2008

(65) Prior Publication Data
US 2009/0263826 A1    Oct. 22, 2009

(30) Foreign Application Priority Data

Aug. 30, 2006   (EP) ..................... 06119780

(51) Int. Cl.
*G01N 33/53* (2006.01)
*G01N 33/00* (2006.01)
*C12M 1/34* (2006.01)

(52) U.S. Cl.
USPC .......... 435/7.1; 435/287.1; 435/4; 435/283.1; 436/96; 436/91

(58) Field of Classification Search
USPC .............. 436/96, 91; 435/7.1, 4, 287.1, 283.1
See application file for complete search history.

(56) References Cited

U.S. PATENT DOCUMENTS

| | | | |
|---|---|---|---|
| 4,540,884 | A | 9/1985 | Stafford et al. |
| 5,397,894 | A | 3/1995 | Wells et al. |
| 7,431,841 | B2 | 10/2008 | Herold et al. |
| 2009/0032462 | A1 | 2/2009 | Herold et al. |

FOREIGN PATENT DOCUMENTS

DE    10203551 A1    8/2003

OTHER PUBLICATIONS

Piro et al. "2-Chlorodeoxyadenosine: An effective new agent for the treatement of chronic lymphocytic leukemia". 1988. Blood. vol. 72. No. 3. pp. 1069-1073.*
Amici et al. "Pyrimidine nucleotidases from human erythrocyte possess phosphotransferase activities specific for pyrimidine nucleotides". FEBS Letters. 1997. vol. 419, pp. 263-267.*
Funato et al. "Myelodysplastic syndrome accompanied by addison's disease and multiple autoimmune phenomena: steroid therapy resolved cytopenias and all immune disorders". Internal Medicine. 2001. vol. 40, Issue 10, p. 1041-1044.*
Krauter, P.W. "Micronucleus Incidence and Hematological Effects in Bullfrog Tadpoles (*Rana catesbeiana*) Exposed to 2-Acetylaminofluorene and 2-Aminofluorene". Arch. Environ. Contam. Toxicol. 1993. vol. 24, pp. 487-493.*
International Search Report issued Sep. 12, 2007 for PCT/EP2007/055472.
Gretener, P., "Reference Values for HanBrl:WIST (SPF) Rats", Version: Aug. 2003.
Kuz'Minskaya, U.A., et al., "Effect of Chlorocamphene on the Isoenzyme Spectrum of Lactate Dehydrogenase in Rat Serum and Liver", Environmental Health Perspectives, vol. 13, 1976, pp. 127-132.
Giglio M.J., et al., "Depressed Plasma Erythropoietin Levels in Rats with Hemodynamically-Mediated Acute Renal Failure", Acta Physiol. Pharmacol Latinoam, vol. 40, 1990, pp. 299-308.
Jelkmann W. et al., "Dependence of Erythropoietin Production on Blood Oxygen Affinity and Hemoglobin Concentration in Rats", Biomed Biochim Acta 46, S, 1987, pp. 304-308.
Wang R-Y, et al., "Effects of Aging on Erythropoietin Secretion in Female Rats", Mechanisms of Ageing and Development, vol. 103, 1998, pp. 81-90.
Niessen, W.M.A. et al., "Liquid Chromatography-Mass Spectrometry General Principles and Instrumentation", Journal of Chromatography A, vol. 703, 1995, pp. 37-57.
Smar. M., et al., "Lyase Activity of Nucleoside 2-Deoxyribosyltransferase: Transient Generation of Ribal and Its Use in the Synthesis of 2'-Deoxynucleosides", Biochemistry, vol. 30, 1991, pp. 7908-7912.
Guzman N., et al., "New Approaches in Clinical Chemistry; On-Line Analyte Concentration and Microreaction Capillary Electrophoresis for the Determination of Drugs, Metabolic Intermediates, and Biopolymers in Biological Fluids", Journal of Chromatography B: vol. 697, 1997, pp. 37-66.

(Continued)

*Primary Examiner* — Christine T Mui
(74) *Attorney, Agent, or Firm* — Novak Druce Connolly Bove + Quigg LLP

(57) ABSTRACT

The present invention relates to a method for diagnosing hemolytic anemia or a predisposition thereof. It also relates to a method of determining whether a compound is capable of inducing hemolytic anemia in a subject and to a method of identifying a drug for treating hemolytic anemia. Furthermore, the present invention relates to a data collection comprising characteristic values of metabolites, a data storage medium comprising said data collection, and a system and a device for diagnosing hemolytic anemia. Finally, the present invention pertains to the use of a group of metabolites or means for the determination thereof for the manufacture of a diagnostic device or composition for diagnosing hemolytic anemia in a subject.

51 Claims, No Drawings

(56) References Cited

OTHER PUBLICATIONS

Jouanin, I. et al. "Adduction of Catechol Estrogens to Nucleosides", Steroids, vol. 67, 2002, pp. 1091-1099.

Dudman, N.P.B., et al. "Radioimmunoassays of Plasma Thymidine, Uridine, Deoxyuridine, and Cytidine/Deoxycytidine", Analytical Biochemistry, vol. 115, 1981, pp. 428-437.

Pruss, A., et al. "Immune Hemolysis-Serological and Clinical Aspects", Clinical and Experimental Medicine, vol. 3, No. 2, 2003, pp. 55-64.

Tattersall, M.H.N., et al. "Plasma Nucleoside Levels", Nucleosides and Cancer Treatment, Proceedings Symposium, 1980, 1981, pp. 71-83.

"International Search Report", issued Sep. 12, 2007 for Application No. PCT/EP2007/055472.

"International Preliminary Report on Patentability", issued on Mar. 12, 2009 for Appln. No. PCT/EP2007/055472.

Carson, D. A., et al., "Specific Toxicity of 2-Chlorodeoxyadenosine Toward Resting and Proliferating Human Lymphocytes", Blood, vol. 62, No. 4, (1983), pp. 737-543.

Singhal, R. L., et al., "Increased Deoxycytindine Kinase Activity in Cancer Cells and Inhibition by Difluorodeoxycytidine", Oncology Research, vol. 4, No. 11/12, (1992), pp. 517-522.

Spasokoukotskaja, T., et al., "Expression of Deoxycytidine Kinase and Phosphorylation of 2-Chlorodeoxyadenosine in Human Normal and Tumour Cells and Tissues", European Journal of Cancer, vol. 31, Issue 2, (1995), pp. 202-208. Abstract.

\* cited by examiner

MEANS AND METHOD FOR DIAGNOSING HEMOLYTIC ANEMIA

RELATED APPLICATIONS

This application is a national stage application (under 35 U.S.C. §371) of PCT/EP2007/055472, filed Jun. 4, 2007, which claims benefit of European application 06119780.2, filed Aug. 30, 2006.

The present invention relates to a method for diagnosing hemolytic anemia or a predisposition thereof. It also relates to a method of determining whether a compound is capable of inducing hemolytic anemia in a subject and to a method of identifying a drug for treating hemolytic anemia. Furthermore, the present invention relates to a data collection comprising characteristic values of metabolites, a data storage medium comprising said data collection, and a system and a device for diagnosing hemolytic anemia. Finally, the present invention pertains to the use of a group of metabolites or means for the determination thereof for the manufacture of a diagnostic device or composition for diagnosing hemolytic anemia in a subject Hemolytic anemia is caused by a increased red blood cell (RBC) destruction. According to the site of this destruction, the hemolytic anemia is divided in an intravascular hemolytic anemia when the hemolysis takes place within the blood vessels, and in an extravascular hemolytic anemia when the hemolysis is performed by phagocytes (above all within the spleen). Hemolytic anemia may be the result of various factors, such as the genetic factors or environmental factors. Environmental factors may be, e.g., contact to toxic compounds as a result of environmental pollution. Compounds known to be inducers of hemolytic hemolytic anemia are, e.g., aromatic amines, hydroxylamine or oximes and their salts. This type of hemolytic anemia is considered to be of the extravascular type.

Hematological, clinical and histopathological parameters are currently used in toxicological studies to diagnose hemolytic anemia. Specifically, hematology parameters which are indicative for hemolytic hemolytic anemia are: Decreased RBC counts, hemoglobin concentration and hematocrit values; Increased mean corpuscular volume (MCV; =macrocytic hemolytic anemia); Often decreased mean corpuscular hemoglobin concentration (MCHC; =hypochromic hemolytic anemia); Increased reticulocyte counts (within 2-3 days); Presence of abnormal red blood cell morphology, e.g. anisocytosis, polychromasia, spherocytes, poikilocytes as well as occurrence of normoblasts, Heinz bodies; White blood cell counts often increased. Parameters for hemolytic anemia derived from the clinical chemistry are: Increased serum bilirubin levels (above all in intravascular hemolytic anemia within 8-10 hours); Increased serum lactate dehydrogenase (isoenzyme 1) activity; Increased free serum hemoglobin and decreased haptoglobin levels (above all with intravascular hemolytic anemia); Increased erythropoietin levels; Hemoglobinuria. Histopathological criteria of hemolytic anemia are: Increased spleen weights characterized by an enlargement of the red pulp and increased red blood cell phagocytosis; Extra-medullar hematopoiesis (above all in liver and spleen); Hemosiderosis (liver, spleen, kidney); Kupffer cell activation in the liver; Increased erythropoiesis in bone marrow.

These changes in clinical pathology parameters occur as a consequence of the red blood cell destruction. There exists no unique marker for diagnosing a hemolytic hemolytic anemia. Many biochemical changes which occur during hemolytic anemia are pathophysiological reactions for the replacement of the destroyed red blood cells (i.e. reticulocytes, abnormal red blood cell morphology, erythropoietin). However, there is a distinct time interval between the event causing hemolysis and the pathophysiological signs becoming overt. Moreover, a significant potency of the hemolysis noxa is necessary to show clinical signs.

Sensitive and specific methods for determining efficiently and reliably hemolytic anemia and, in particular, the early onset or a predisposition thereof are not available but would, nevertheless, be highly appreciated.

Accordingly, the technical problem underlying the present invention could be seen as the provision of means and methods for efficiently and reliably diagnosing hemolytic anemia and/or a predisposition therefor. The technical problem is solved by the embodiments characterized in the claims and described herein below.

Thus, the present invention relates to a method for diagnosing hemolytic anemia or a predisposition thereof comprising:
(a) determining the amount of deoxycytidine in a test sample of a subject suspected to suffer from hemolytic anemia or to have a predisposition therefor; and
(b) comparing the amount determined in step (a) to a reference, whereby hemolytic anemia or a predisposition therefor is to be diagnosed.

The expression "method for diagnosing" as referred to in accordance with the present invention means that the method either essentially consists of the aforementioned steps or may include further steps. However, it is to be understood that the method, in a preferred embodiment, is a method carried out ex vivo, i.e. not practised on the human or animal body. Diagnosing as used herein refers to assessing the probability according to which a subject is suffering from a disease. As will be understood by those skilled in the art, such an assessment, although preferred to be, may usually not be correct for 100% of the subjects to be diagnosed. The term, however, requires that a statistically significant portion of subjects can be identified as suffering from the disease or as having a predisposition therefor. Whether a portion is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 50%, at least 60%, at least 70%, at least 80%, at least 90%, at least 95%. The p-values are, preferably, 0.2, 0.1, 0.05.

Diagnosing according to the present invention includes monitoring, confirmation, and classification of the relevant disease or its symptoms. Monitoring relates to keeping track of an already diagnosed disease, e.g. to analyze the progression of the disease, the influence of a particular treatment on the progression of disease or complications arising during the disease period or after successful treatment of the disease. Confirmation relates to the strengthening or substantiating a diagnosis already performed using other indicators or markers. Classification relates to allocating the diagnosis according to the strength or kind of symptoms into different classes.

The term "hemolytic anemia" refers to a pathophysiological condition in a subject characterized by a decreased amount of red blood cells. Preferably, hemolytic anemia as used herein can be characterized by haematological, clinical pathology and histopathological parameters. Hematological parameters indicative for hemolytic anemia are: Decreased RBC counts, hemoglobin concentration and hematocrit values; Increased mean corpuscular volume (MCV; =macrocytic hemolytic anemia); Optionally, decreased mean corpuscular hemoglobin concentration (MCHC; =hypochromic hemolytic anemia); Increased reticulocyte counts (within 2-3 days); Presence of abnormal red blood cell morphology, e.g. anisocytosis, polychromasia, spherocytes, poikilocytes, normoblasts, Heinz bodies; White blood cell counts optionally increased. Parameters for hemolytic anemia derived from the clinical chemistry are: Increased serum bilirubin levels (above all in intravascular hemolytic anemia within 8-10 hours); Increased serum lactate dehydrogenase (isoenzyme 1) activity; Increased free serum hemoglobin and decreased haptoglobin levels (above all with intravascular hemolytic anemia); Increased erythropoietin levels; Hemoglobinuria. Histopathological criteria of hemolytic anemia are: Increased spleen weights characterized, e.g., by an enlargement of the red pulp and increased red blood cell phagocytosis; Extramedullar hematopoiesis (above all in liver and spleen); Hemosiderosis (liver, spleen, kidney); Kupffer cell activation in the liver; Increased erythropoiesis in bone marrow. More preferably, the haemolytic hemolytic anemia is extravascular haemolytic hemolytic anemia. Most preferably, it is caused by aromatic amines, oximes or hydroxlyamines as well as salts thereof or resembles the biochemical and physiological parameters of said type of hemolytic anemia.

Reference values of hematological parameters indicative for anemia in humans are given in the following Table 1:

TABLE 1

| Parameter | Unit | Reference value | Remark |
|---|---|---|---|
| RBC | T/L | Males: 4.5-5.9 | |
| | | Females: 4.1-5.1 | |
| Hb | g/dL | Males: >13.0 | |
| | | Females: >12.0 | |
| Hematocrit | % | Males: 36.0-48.2 | |
| | | Females: 34.7-44.7 | |
| MCV | μm$^3$ | 80-96 | |
| MCHC | g/dL | 33-36 | |
| Retikulocytes | % | 0.5-2 | |
| WBC | G/L | 4.4-11.3 | |
| Bilirubin | μmol/L | 2-21 | |
| LDH, total | U/L | 135-315 | IFCC (37° C.) |
| LDH$_1$ | % | 15-23 | Agarose gelelektrophoresis |
| Free hemoglobin in serum | mg/L | <20 | |
| Haptoglobin | mg/dL | >20 | CRM470/RM002 Standard |
| Erythropoetin | U/L | 6-25 | 2. IRP B Standard |

Reference values of hematological parameters indicative for anemia in rodents as exemplified for the rat are given in the following Table 2:

TABLE 2

| Parameter | Unit | Number of Samples | Reference Range | Remarks |
|---|---|---|---|---|
| RBC | T/L | 734 | Male: 7.7-9.0 | Ref. 1 |
| | | 690 | Female: 7.3-8.6 | |
| Hb | mmol/L | 734 | Male: >9.2 | Ref. 1 |
| | | 690 | Female: >8.7 | |
| Haematocrit | % | 734 | Male: 43.8-50.4 | Ref. 1 |
| | | 690 | Females: 41.0-47.2 | |
| MCV | μm$^3$ | 1424 | 53-60 | Ref. 1 |
| MCHC | mmol/L | 1424 | 19.8-22.5 | Ref. 1 |
| Reticulozytes | % | 804 | 2-4 | Ref. 1 |
| WBC | G/L | 734 | Male: 5.0-10.6 | Ref. 1 |
| | | 690 | Female: 3.3-7.8 | |
| Bilirubin, total | μmol/L | 695 | Male: 0.8-2.0 | Ref. 1 |
| | | 683 | Female: 1.0-2.4 | |

TABLE 2-continued

| Parameter | Unit | Number of Samples | Reference Range | Remarks |
|---|---|---|---|---|
| LDH, total | U/L | 791 | 76-233 | Ref. 1, IFCC (37° C.) |
| LDH$_1$ | % | 10 | 7.6-10 | Ref. 2 |
| Free Hb in serum | mg/L | | No values for rats | |
| Haptoglobin | mg/dL | | No values for rats | |
| Erythropoëtin | U/L | | 17-25 | Ref. 3-5 |

References:
1. Gretener, P., Reference Values for HanBrl:WIST (SPF) Rats, version August 2003
2. Kuz'minskaya, U.A. and Alekhina, S.M. Effect of Chlorocamphene on the Isoenzyme Spectrum of Lactate Dehydrogenase in the Rat Serum and Liver. Environmental Health Perspectives, 13: 127-132, 1976
3. Giglio J. et al., Depressed Plasma Erythropoietin levels in rats with hemodynamically-mediated acute renal failure, Acta Physiol. Pharmacol Latinoam. 40, 299-308, 1990
4. Jelkmann W. et al, Dependence of erythropoietin production on blood oxygen affinity and hemoglbin concentration in rats, Biomed Biochim Acta 46, S304-308, 1987
5. Wang R-Y et al., Effects of aging on erythropoietin secretion in female rats, Mechanisms of Ageing and Development 103, 81-90, 1998

The term "predisposition" as used herein means that a subject has not yet developed the disease or any of the aforementioned disease symptoms or other diagnostic criteria but, nevertheless, will develop the disease in the future with a certain likelihood within a predetermined prognostic window. The predictive window is an interval in which the subject shall develop haemolytic anemia according to the predicted likelihood. The predictive window may be the entire remaining lifespan of the subject upon analysis by the method of the present invention. Preferably, however, the predictive window is an interval of one month, six months or one, two, three, four, five or ten years after the sample to be analyzed by the method of the present invention has been obtained. In case of a predisposition, the said likelihood shall differ significantly from the likelihood of statistical appearance of haemolytic anemia. Preferably, the likelihood for developing haemolytic anemia is at least 30%, at least 40%, at least 50%, at least 60%, at least 70%, at least 80%, at least 90% or 100%. Diagnosis of a predisposition may sometimes be referred to as prognosis or prediction of the likelihood that a subject will develop the disease.

The term "deoxycytidine" as used herein refers, preferably, to a metabolite having a chemical structure as disclosed in the following formula A:

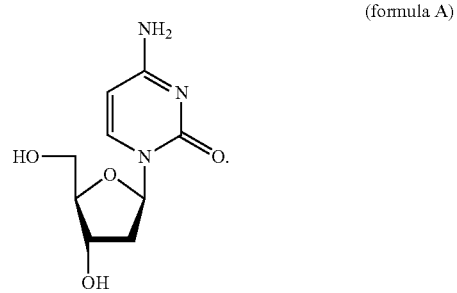 [SMILES: Nc1ccn([C@H]2C[C@@H](O)[C@@H](CO)O2)c(=O)n1]

(formula A)

It is to be understood that in the method of the present invention, metabolites in addition to deoxycytidine may be, preferably, determined. A metabolite as used herein refers to at least one molecule of a specific metabolite up to a plurality of molecules of the said specific metabolite. It is to be understood further that a group of metabolites means a plurality of chemically different molecules wherein for each metabolite at least one molecule up to a plurality of molecules may be present. A metabolite in accordance with the present invention encompasses all classes of organic or inorganic chemical compounds including those being comprised by biological material such as organisms. Preferably, the metabolite in accordance with the present invention is a small molecule compound. More preferably, in case a plurality of metabolites is envisaged, said plurality of metabolites representing a metabolome, i.e. the collection of metabolites being comprised by an organism, an organ, a tissue or a cell at a specific time and under specific conditions.

The metabolites are small molecule compounds, such as substrates for enzymes of metabolic pathways, intermediates of such pathways or the products obtained by a metabolic pathway. Metabolic pathways are well known in the art and may vary between species. Preferably, said pathways include at least citric acid cycle, respiratory chain, photosynthesis, photorespiration, glycolysis, gluconeogenesis, hexose monophosphate pathway, oxidative pentose phosphate pathway, production and β-oxidation of fatty acids, urea cycle, amino acid biosynthesis pathways, protein degradation pathways such as proteasomal degradation, amino acid degrading pathways, biosynthesis or degradation of: lipids, polyketides (including e.g. flavonoids and isoflavonoids), isoprenoids (including eg. terpenes, sterols, steroids, carotenoids, xanthophylls), carbohydrates, phenylpropanoids and derivatives, alcaloids, benzenoids, indoles, indole-sulfur compounds, porphyrines, anthocyans, hormones, vitamins, cofactors such as prosthetic groups or electron carriers, lignin, glucosinolates, purines, pyrimidines, nucleosides, nucleotides and related molecules such as tRNAs, microRNAs (miRNA) or mRNAs. Accordingly, small molecule compound metabolites are preferably composed of the following classes of compounds: alcohols, alkanes, alkenes, alkines, aromatic compounds, ketones, aldehydes, carboxylic acids, esters, amines, imines, amides, cyanides, amino acids, peptides, thiols, thioesters, phosphate esters, sulfate esters, thioethers, sulfoxides, ethers, or combinations or derivatives of the aforementioned compounds. The small molecules among the metabolites may be primary metabolites which are required for normal cellular function, organ function or animal growth, development or health. Moreover, small molecule metabolites further comprise secondary metabolites having essential ecological function, e.g. metabolites which allow an organism to adapt to its environment. Furthermore, metabolites are not limited to said primary and secondary metabolites and further encompass artificial small molecule compounds. Said artificial small molecule compounds are derived from exogenously provided small molecules which are administered or taken up by an organism but are not primary or secondary metabolites as defined above. For instance, artificial small molecule compounds may be metabolic products obtained from drugs by metabolic pathways of the animal. Moreover, metabolites further include peptides, oligopeptides, polypeptides, oligonucleotides and polynucleotides, such as RNA or DNA. More preferably, a metabolite has a molecular weight of 50 Da (Dalton) to 30,000 Da, most preferably less than 30,000 Da, less than 20,000 Da, less than 15,000 Da, less than 10,000 Da, less than 8,000 Da, less than 7,000 Da, less than 6,000 Da, less than 5,000 Da, less than 4,000 Da, less than 3,000 Da, less than 2,000 Da, less than 1,000 Da, less than 500 Da, less than 300 Da, less than 200 Da, less than 100 Da. Preferably, a metabolite has, however, a molecular weight of at least 50 Da. Most preferably, a metabolite in accordance with the present invention has a molecular weight of 50 Da up to 1,500 Da.

Preferred metabolites to be determined by the method of the present invention in addition to deoxycytidine are adrenal corticosteroides. Specifically, it is envisaged that the in accordance with the present invention at least one adrenal corticosteroide is to be determined in addition. The term "adrenal corticosteroides" as used herein, preferably, encompasses 18-hydroxycorticosterone, aldosteron, 11-desoxycortisol, cortisol and cortisone. In case the subject to be investigated is a human, the said at least one adrenal corticosteroide is, preferably, cortisol. In case the subject to be investigated is a rodent, the said at least one adrenal corticosteroide is, preferably, 18-hydroxycorticosterone or 11-desoxycortisol and, more preferably, both adrenal corticosteroides are to be determined. If 18-hydroxycorticosterone and 11-desoxycortisol are determined together, it is, more preferably, envisaged that the determination is carried out by NMR-based techniques or antibody-based techniques such as ELISA or LC-MS/MS.

The term "test sample" as used herein refers to samples to be used for the diagnosis of hemolytic anemia or a predisposition therefor by the method of the present invention. Said test sample is a biological sample. Samples from biological sources (i.e. biological samples) usually comprise a plurality of metabolites. Preferred biological samples to be used in the method of the present invention are samples from body fluids, preferably, blood, plasma, serum, saliva, urine or cerebrospinal fluid, or samples derived, e.g., by biopsy, from cells, tissues or organs. More preferably, the sample is a blood, plasma or serum sample, most preferably, a plasma sample. Biological samples are derived from a subject as specified elsewhere herein. Techniques for obtaining the aforementioned different types of biological samples are well known in the art. For example, blood samples may be obtained by blood taking while tissue or organ samples are to be obtained, e.g., by biopsy.

The aforementioned samples are, preferably, pre-treated before they are used for the method of the present invention. As described in more detail below, said pre-treatment may include treatments required to release or separate the compounds or to remove excessive material or waste. Suitable techniques comprise centrifugation, extraction, fractioning, ultrafiltration, protein precipitation followed by filtration and purification and/or enrichment of compounds. Moreover, other pre-treatments are carried out in order to provide the compounds in a form or concentration suitable for compound analysis. For example, if gas-chromatography coupled mass spectrometry is used in the method of the present invention, it will be required to derivatize the compounds prior to the said gas chromatography. Suitable and necessary pre-treatments depend on the means used for carrying out the method of the invention and are well known to the person skilled in the art. Pre-treated samples as described before are also comprised by the term "sample" as used in accordance with the present invention.

The term "subject" as used herein relates to animals, preferably to mammals such as mice, rats, guinea pigs, rabbits, hamsters, pigs, sheep, dogs, cats, horses, monkeys, or cows and, also preferably, to humans. More preferably, the subject is a rodent and, most preferably, a rat. Other animals which may be diagnosed applying the method of the present invention are fishes, birds or reptiles. Preferably, said subject was in or has been brought into contact with a compound suspected to be capable of inducing hemolytic anemia. A subject which has been brought into contact with a compound suspected to induce hemolytic anemia may, e.g., be a laboratory animal such as a rat which is used in a screening assay for, e.g., toxicity of compounds. A subject suspected to have been in contact with a compound capable of inducing hemolytic anemia may be a subject to be diagnosed for selecting a suitable therapy. Preferably, a compound capable of inducing hemolytic anemia as used herein refers to aromatic amines or hydroxylamines.

The term "determining the amount" as used herein refers to determining at least one characteristic feature of an aforementioned metabolite comprised by the sample referred to herein. Characteristic features in accordance with the present invention are features which characterize the physical and/or chemical properties including biochemical properties of a metabolite. Such properties include, e.g., molecular weight, viscosity, density, electrical charge, spin, optical activity, colour, fluorescence, chemoluminescence, elementary composition, chemical structure, capability to react with other compounds, capability to elicit a response in a biological read out system (e.g., induction of a reporter gene) and the like. Values for said properties may serve as characteristic features and can be determined by techniques well known in the art. Moreover, the characteristic feature may be any feature which is derived from the values of the physical and/or chemical properties of a metabolite by standard operations, e.g., mathematical calculations such as multiplication, division or logarithmic calculus. Most preferably, the at least one characteristic feature allows the determination and/or chemical identification of the said at least one metabolite and its amount. Accordingly, the characteristic value, preferably, also comprises information relating to the abundance of the metabolite from which the characteristic value is derived. For example, a characteristic value of a metabolite may be a peak in a mass spectrum. Such a peak contains characteristic information of the metabolite, i.e. the mass-to-charge ratio (m/z) information, as well as an intensity value being related to the abundance of the said metabolite (i.e. its amount) in the sample.

As discussed before, the aforementioned metabolite or metabolites comprised by a test sample may be, preferably, determined in accordance with the present invention quantitatively or semi-quantitatively. For quantitative determination, either the absolute or precise amount of the metabolite will be determined or the relative amount of the metabolite will be determined based on the value determined for the characteristic feature(s) referred to herein above. The relative amount may be determined in a case were the precise amount of a metabolite can or shall not be determined. In said case, it can be determined whether the amount in which the metabolite is present is enlarged or diminished with respect to a second sample comprising said metabolite in a second amount. Quantitatively analysing a metabolite, thus, also includes what is sometimes referred to as semi-quantitative analysis of a metabolite.

Moreover, determining as used in the method of the present invention, preferably, includes using a compound separation step prior to the analysis step referred to before. Preferably, said compound separation step yields a time resolved separation of the metabolites comprised by the sample. Suitable techniques for separation to be used preferably in accordance with the present invention, therefore, include all chromatographic separation techniques such as liquid chromatography (LC), high performance liquid chromatography (HPLC), gas chromatography (GC), thin layer chromatography, size exclusion or affinity chromatography. These techniques are well known in the art and can be applied by the person skilled in the art without further ado. Most preferably, LC and/or GC are chromatographic techniques to be envisaged by the method of the present invention. Suitable devices for such determination of metabolites are well known in the art. Preferably, mass spectrometry is used in particular gas chromatography mass spectrometry (GC-MS), liquid chromatography mass spectrometry (LC-MS), direct infusion mass spectrometry or Fourier transform ion-cyclotrone-resonance mass spectrometry (FT-ICR-MS), capillary electrophoresis mass spectrometry (CE-MS), high-performance liquid chromatography coupled mass spectrometry (HPLC-MS), quadrupole mass spectrometry, any sequentially coupled mass spectrometry, such as MS-MS or MS-MS-MS, inductively coupled plasma mass spectrometry (ICP-MS), pyrolysis mass spectrometry (Py-MS), ion mobility mass spectrometry or time of flight mass spectrometry (TOF). Most preferably, LC-MS and/or GC-MS are used as described in detail below. Said techniques are disclosed in, e.g., Nissen, Journal of Chromatography A, 703, 1995: 37-57, U.S. Pat. No. 4,540,884 or U.S. Pat. No. 5,397,894, the disclosure content of which is hereby incorporated by reference. As an alternative or in addition to mass spectrometry techniques, the following techniques may be used for compound determination: nuclear magnetic resonance (NMR), magnetic resonance imaging (MRI), Fourier transform infrared analysis (FT-IR), ultraviolet (UV) spectroscopy, refraction index (RI), fluorescent detection, radiochemical detection, electrochemical detection, light scattering (LS), dispersive Raman spectroscopy or flame ionisation detection (FID). These techniques are well known to the person skilled in the art and can be applied without further ado. The method of the present invention shall be, preferably, assisted by automation. For example, sample processing or pre-treatment can be automated by robotics. Data processing and comparison is, preferably, assisted by suitable computer programs and databases. Automation as described herein before allows using the method of the present invention in high-throughput approaches.

Moreover, the metabolite can also be determined by a specific chemical or biological assay. Said assay shall comprise means which allow to specifically detect the at least one metabolite in the sample. Preferably, said means are capable of specifically recognizing the chemical structure of the metabolite or are capable of specifically identifying the metabolite based on its capability to react with other compounds or its capability to elicit a response in a biological read out system (e.g., induction of a reporter gene). Means which are capable of specifically recognizing the chemical structure of a metabolite are, preferably, antibodies or other proteins which specifically interact with chemical structures, such as receptors or enzymes. Specific antibodies, for instance, may be obtained using the metabolite as antigen by methods well known in the art. Antibodies as referred to herein include both polyclonal and monoclonal antibodies, as well as fragments thereof, such as Fv, Fab and $F(ab)_2$ fragments that are capable of binding the antigen or hapten. The present invention also includes humanized hybrid antibodies wherein amino acid sequences of a non-human donor antibody exhibiting a desired antigen-specificity are combined with sequences of a human acceptor antibody. Moreover, encompassed are single chain antibodies. The donor sequences will usually include at least the antigen-binding amino acid residues of the donor but may comprise other structurally and/or functionally relevant amino acid residues of the donor antibody as well. Such hybrids can be prepared by several methods well known in the art. Suitable proteins which are capable of specifically recognizing the metabolite are, preferably, enzymes which are involved in the metabolic conversion of the said metabolite. Said enzymes may either use the metabolite as a substrate or may convert a substrate into the metabolite. Moreover, said antibodies may be used as a basis to generate oligopeptides which specifically recognize the metabolite. These oligopeptides shall, for example, comprise the enzyme's binding domains or pockets for the said metabolite. Suitable antibody and/or enzyme based assays may be RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immuno assay (DELFIA) or solid phase immune tests. Moreover, the metabolite may also be identified based on its capability to react with other compounds, i.e. by a specific chemical reaction. Further, the metabolite may be determined in a sample due to its capability to elicit a response in a biological read out system. The biological response shall be detected as read out indicating the presence and/or the amount of the metabolite comprised by the sample. The biological response may be, e.g., the induction of gene expression or a phenotypic response of a cell or an organism.

Moreover, depending on the technique used for determining the amount of a metabolite, the analyte which is determined by the determination technique may differ with respect to its chemical nature from the metabolite found in the sample. Such analytes include derivatives of the metabolites which are generated by the pre-treatment processes used for the sample or by the determination technique as such. However, it is to be understood that the said derivatives of the metabolite which are determined (i.e. which are analytes) qualitatively and quantitatively represent the metabolite. For deoxycytidine referred to above, cytosine and/or ribal (1,4-anhydro-2-deoxy-D-erythro-pent-1-enitol) are suitable analytes, in particular, if mass spectrometry based techniques and, more preferably, LC-MS and/or GC-MS as described herein, are used as determination techniques. Accordingly, in order to diagnose hemolytic anemia or a predisposition therefor, the amounts of cytosine and/or ribal can be, preferably, determined as a substitute for deoxycytidine and compared to suitable references whereby the hemolytic anemia or a predisposition therefor will be diagnosed as referred herein. Cytosine and ribal (also called "MetID 407" herein below) have been found to be analytes of a rat plasma sample if detected with GC/MS analysis with application of an electron impact mass spectrometry at 70 eV and after derivatisation with 2% O-methylhydroxylamine-hydrochlorid in pyridine and subsequently with N-methyl-N-trimethylsilyltrifluoracetamid. Ribal was identified by following characteristic nominal masses (relative ratios): 170 (100+/−20%), 169 (90+/−20%), 155 (64+/−20%), 103 (34+/−20%), 127 (18+/−20%). The chemical structures of cytosine and ribal are well known in the art; see, e.g., Smar 1991, Biochemistry 30: 7908-7912.

The term "reference" refers to values of characteristic features of the metabolites which can be correlated to hemolytic anemia or a predisposition therefor. Such reference results are, preferably, obtained from a sample derived from a (i) subject which has been brought into contact with aromatic amines, oximes or hydroxylamines or (ii) a subject which suffers from extravascular hemolytic anemia or which has a predisposition therefor. A subject may be brought into contact with aromatic amines, oximes or hydroxylamines by each topic or systemic administration mode as long as the aromatic amines, oximes or hydroxylamines are bioavailable. The reference results may be determined as described hereinabove for the amounts of the metabolites. Alternatively, but nevertheless also preferred, the reference results may be obtained from sample derived from (i) a subject which has not been brought into contact with aromatic amines, oximes or hydroxylamines or (ii) a subject known to not suffer from extravascular hemolytic anemia or having predisposition therefor, i.e. a healthy subject with respect to hemolytic anemia and, more preferably, other diseases as well. Moreover, the reference, also preferably, could be a calculated reference, most preferably, the average or median, for the relative or absolute amount for a metabolite derived from a population of individuals comprising the subject to be investigated. However, it is to be understood that the population of subjects to be investigated for determining a calculated reference, preferably, either consist of apparently healthy subjects (e.g. untreated) or comprise a number of apparently healthy subjects which is large enough to be statistically resistant against significant average or median changes due to the presence of the test subject(s) in the said population. The absolute or relative amounts of the metabolites of said individuals of the population can be determined as specified elsewhere herein. How to calculate a suitable reference value, preferably, the average or median, is well known in the art. The population of subjects referred to before shall comprise a plurality of subjects, preferably, at least 5, 10, 50, 100, 1,000 or 10,000 subjects. It is to be understood that the subject to be diagnosed by the method of the present invention and the subjects of the said plurality of subjects are of the same species.

More preferably, the reference results, i.e. values for at least one characteristic features of a metabolite, will be stored in a suitable data storage medium such as a database and are, thus, also available for future diagnoses. This also allows efficiently diagnosing predisposition for a disease because suitable reference results can be identified in the database once it has been confirmed (in the future) that the subject from which the corresponding reference sample was obtained (indeed) developed hemolytic anemia.

The term "comparing" refers to assessing whether the results of the determination described hereinabove in detail, i.e. the results of the qualitative or quantitative determination of a metabolite, are identical or similar to reference results or differ therefrom.

In case the reference results are obtained from a sample derived from a (i) subject which has been brought into contact with aromatic amines, oximes or hydroxylamines or (ii) a subject which suffers from extravascular hemolytic anemia or which has predisposition therefor, the hemolytic anemia or predisposition can be diagnosed based on the degree of identity or similarity between the test results obtained from the test sample and the aforementioned reference results, i.e. based on an identical or similar qualitative or quantitative composition with respect to the aforementioned metabolites. The results of the test sample and the reference results are identical, if the values for the characteristic features and, in the case of quantitative determination, the intensity values are identical. Said results are similar, if the values of the characteristic features are identical but the intensity values are different. Such a difference is, preferably, not significant and shall be characterized in that the values for the intensity are within at least the interval between $1^{st}$ and $99^{th}$ percentile, $5^{th}$ and $95^{th}$ percentile, $10^{th}$ and $90^{th}$ percentile, $20^{th}$ and $80^{th}$ percentile, $30^{th}$ and $70^{th}$ percentile, $40^{th}$ and $60^{th}$ percentile of the reference value. the $50^{th}$, $60^{th}$, $70^{th}$, $80^{th}$, $90^{th}$ or $95^{th}$ percentile of the reference value.

In case the reference results are obtained (i) a subject which has not been brought into contact with aromatic amines, oximes or hydroxylamines or (ii) a subject known to not suffer from extravascular hemolytic anemia or having predisposition therefor, the hemolytic anemia or predisposition can be diagnosed based on the differences between the test results obtained from the test sample and the aforementioned reference results, i.e. differences in the qualitative or quantitative composition with respect to the aforementioned metabolites. The same applies if a calculated reference as specified above is used. The difference may be an increase in the absolute or relative amount of a metabolite (sometimes referred to as up-regulation of the metabolite; see also Examples) or a decrease in either of said amounts or the absence of a detectable amount of the metabolite (sometimes referred to as up-regulation of the metabolite; see also Examples). Preferably, the difference in the relative or absolute amount is significant, i.e. outside of the interval between $45^{th}$ and $55^{th}$ percentile, $40^{th}$ and $60^{th}$ percentile, $30^{th}$ and $70^{th}$ percentile, $20^{th}$ and $80^{th}$ percentile, $10^{th}$ and $90^{th}$ percentile, $5^{th}$ and $95^{th}$ percentile, $1^{st}$ and $99^{th}$ percentile of the reference value. Specifically, an increased amount of deoxycytidine or its analytes cytosine and/or ribal in comparison to the reference obtained from (i) a subject which has not been brought into contact with aromatic amines, oximes or hydroxylamines or (ii) a subject known to not suffer from extravascular hemolytic anemia or having predisposition therefore or a calculated reference are indicative for hemolytic anemia. Moreover, if the said at least adrenal corticosteroid (e.g., cortisol, aldosteron, cortisone, 18-hydroxycorticosterone or 11-desoxycortisol) has been determined in addition, a decreased amount of the at least one adrenal corticosteroid in comparison to the said reference is indicative for haemolytic anemia.

For the specific metabolites referred to in this specification, preferred values for the changes in the relative amounts (i.e. "fold"-changes) or the kind of change (i.e. "up"- or "down"-regulation resulting in a higher or lower relative and/or absolute amount) are indicated in the following Table 3 and in the Examples below. If it is indicated in said table that a given metabolite is "up-regulated" in a subject, the relative and/or absolute amount will be increased, if it is "down-regulated", the relative and/or absolute amount of the metabolite will be decreased. Moreover, the "fold"-change indicates the degree of increase or decrease, e.g., a 2-fold increase means that the amount is twice the amount of the metabolite compared to the reference.

TABLE 3

| Metabolite | Regulation | Fold change against controls (males/females) |
|---|---|---|
| 18-hydroxycorticosterone | down | 0.18*/0.47* |
| 11-desoxycortisol | down | 0.27*/0.41* |
| Cytosine** | up | 1.71*/1.38 |
| ribal (1,4-anhydro-2-deoxy-D-erythro-pent-1-enitol) (=MetID 407)** | up | 1.82*/1.59* |

*statistically significant with p ≤ 0.05 (Student's t-test)
**whereby the analytes cytosine and ribal represent the metabolite deoxycytidine The comparison is, preferably, assisted by automation. For example, a suitable computer program comprising algorithm for the comparison of two different data sets (e.g., data sets comprising the values of the characteristic feature(s)) may be used. Such computer programs and algorithm are well known in the art. Notwithstanding the above, a comparison can also be carried out manually.

The aforementioned methods for the determination of metabolite(s) can be implemented into a device. A device as used herein shall comprise at least the aforementioned means. Moreover, the device, preferably, further comprises means for comparison and evaluation of the detected characteristic feature(s) of a metabolite and, also preferably, the determined signal intensity. The means of the device are, preferably, operatively linked to each other. How to link the means in an operating manner will depend on the type of means included into the device. For example, where means for automatically qualitatively or quantitatively determining a metabolite are applied, the data obtained by said automatically operating means can be processed by, e.g., a computer program in order to facilitate the diagnosis. Preferably, the means are comprised by a single device in such a case. Said device may accordingly include an analyzing unit for the metabolites and a computer unit for processing the resulting data for the diagnosis. Alternatively, where means such as test stripes are used for determining the metabolites, the means for diagnosing may comprise control stripes or tables allocating the determined result data to result data known to be accompanied with hemolytic anemia or those being indicative for a healthy subject as discussed above. Preferred devices are those which can be applied without the particular knowledge of a specialized clinician, e.g., test stripes or electronic devices which merely require loading with a sample.

Alternatively, the methods for the determination of the metabolite(s) can be implemented into a system comprising several devices which are, preferably, operatively linked to each other. Specifically, the means must be linked in a manner as to allow carrying out the method of the present invention as described in detail above. Therefore, operatively linked, as used herein, preferably, means functionally linked. Depending on the means to be used for the system of the present invention, said means may be functionally linked by connecting each mean with the other by means which allow data transport in between said means, e.g., glass fiber cables, and other cables for high throughput data transport. Nevertheless, wireless data transfer between the means is also envisaged by the present invention, e.g., via a LAN (including Wireless LAN, W-LAN). A preferred system comprises means for determining metabolites. Means for determining metabolites as used herein encompass means for separating metabolites, such as chromatographic devices, and means for metabolite determination, such as mass spectrometry devices. Suitable devices have been described in detail above. Preferred means for compound separation to be used in the system of the present invention include chromatographic devices, more preferably devices for liquid chromatography, HPLC, and/or gas chromatography. Preferred devices for compound determination comprise mass spectrometry devices, more preferably, GC-MS, LC-MS, direct infusion mass spectrometry, FT-ICR-MS, CE-MS, HPLC-MS, quadrupole mass spectrometry, sequentially coupled mass spectrometry (including MS-MS or MS-MS-MS), ICP-MS, Py-MS or TOF. The separation and determination means are, preferably, coupled to each other. Most preferably, LC-MS and/or GC-MS is used in the system of the present invention as described in detail elsewhere in the specification. Further comprised shall be means for comparing and/or analyzing the results obtained from the means for determination of metabolites. The means for comparing and/or analyzing the results may comprise at least one databases and an implemented computer program for comparison of the results. Preferred embodiments of the aforementioned systems and devices are also described in detail below.

Advantageously, it has been found in the study underlying the present invention that the amount of deoxycytidine serves as a biomarker for hemolytic anemia, specifically hemolytic anemia induced by aromatic amines, oximes and hydroxylamines. In addition to the aforementioned metabolite, at least one adrenal corticosteroid can be determined whereby the specificity and accuracy of the method will be even more improved. A change in the quantitative and/or qualitative composition of the metabolome with respect to these specific metabolites is indicative for hemolytic anemia or a predisposition therefor. The haematological parameters which are currently used for diagnosing hemolytic anemia are less specific and less sensitive in comparison to the biomarker determination provided by the present invention. Thanks to the present invention, hemolytic anemia can be more efficiently and reliably diagnosed—even before the symptoms of the disease become apparent. Moreover, based on the aforementioned findings, screening for compounds which are suspected to be capable of inducing hemolytic anemia has become possible, e.g., in the context of toxicological assessments. Further, the findings are the basis for screening assays for drugs which are useful for the therapy of hemolytic anemia.

Therefore, the present invention also relates to a method of determining whether a compound is capable of inducing hemolytic anemia in a subject comprising:

(a) determining in a sample of a subject which has been brought into contact with a compound suspected to be capable of inducing hemolytic anemia the amount of deoxycytidine or its analytes cytosine and/or ribal; and (b) comparing the amount determined in step (a) to a reference, whereby the capability of the compound to induce hemolytic anemia is determined.

Moreover, the present invention also encompasses a method of identifying a substance for treating hemolytic anemia comprising the steps of:

(a) determining in a sample of a subject suffering from hemolytic anemia which has been brought into contact with a candidate substance for treating hemolytic anemia the amount of deoxycytidine or its analytes cytosine and/or ribal; and (b) comparing the amount determined in step (a) to a reference, whereby the said substance is to be identified.

All definitions and explanations of the terms made above apply mutatis mutandis for the aforementioned methods and all other embodiments described further below except stated otherwise in the following. Specifically, in case of the method of identifying a substance useful for treating hemolytic anemia, said reference is, preferably, derived from (i) a subject which has been brought into contact with aromatic amines, oximes or hydroxylamins or (ii) a subject which suffers from extravascular hemolytic anemia. More preferably, amounts for the metabolites which differ in the test sample and the reference are indicative for a substance useful for treating hemolytic anemia. Specifically, a decreased amount of deoxycytidine (or its analytes cytosine and/or ribal) in comparison to the reference is indicative for a drug for treating hemolytic anemia. Moreover, if the said at least one glucocorticoide (e.g., cortisol, cortisone, aldosteron, 18-hydroxycorticosterone or 11-desoxycortisol) has been determined in addition, an increased amount of the at least one glucocorticoide in comparison to the said reference is indicative for a substance useful for treating haemolytic anemia. Alternatively, the said reference may be, preferably, be derived from (i) a subject which has not been brought into contact with aromatic amines, oximes or hydroxylamines or (ii) a subject known to not suffer from extravascular hemolytic anemia or a predisposition therefore or may be a calculated reference for the metabolites in a population of subjects. If such a reference is used, identical or similar amounts for the metabolites in the test sample and the reference are indicative for a substance useful for treating haemolytic anemia.

The term "substance for treating hemolytic anemia" refers to compounds which may directly interfere with the hemolytic cascades induced during hemolytic anemia. Accordingly, the activity of hemolytic enzymes may be inhibited. Alternatively, it is envisaged that substances may affect the hemolytic cascade indirectly by, e.g., modulating the expression of hemolytic enzymes or other factors required for hemolysis during hemolytic anemia. The substances referred to herein above may act antagonistically, i.e. by counteracting the effects of the hemolytic enzymes or other factors. Substances to be screened by the method of the present invention may be organic and inorganic chemicals, such as small molecules, polynucleotides, oligonucleotides, peptides, polypeptides including antibodies or other artificial or biological polymers. Preferably, the substances are suitable as drugs, pro-drugs or lead substances for the development of drugs or pro-drugs.

It is to be understood that if the methods of the present invention are to be used for identifying drugs for the therapy of hemolytic anemia or for toxicological assessments of compounds (i.e. determining whether a compound is capable of inducing hemolytic anemia), test samples of a plurality of subjects may be investigated for statistical reasons. Preferably, the metabolome within such a cohort of test subjects shall be as similar as possible in order to avoid differences which are caused, e.g., by factors other than the compound to be investigated. Subjects to be used for the said methods are, preferably, laboratory animals such as rodents and, more preferably, rats. It is to be understood further that the said laboratory animals shall be, preferably, sacrificed after completion of the method of the present invention. All subjects of a cohort test and reference animals shall be kept under identical conditions to avoid any differential environmental influences. Preferred conditions for rats which have an essentially identical metabolome can be provided by compiling an animal population being of essentially the same age and keeping said animal population for a time period sufficient for acclimatization under the following housing conditions: (i) constant temperature, (ii) constant humidity, (iii) physical separation of the animals of the animal population, (iv) feeding ad libitum, wherein the food to be fed is essentially free of chemical or microbial contaminants, (v) drinking liquid ad libitum, wherein the drinking liquid is essentially free of chemical or microbial contaminants, (vi) constant illumination period, and providing the animal population after said time period. Compiling, as referred to above, means to select the animals from any source to establish the animal population to be subjected to the method of the present invention. Accordingly, the animals may be progeny of the same mother animal or progeny of different mother animals. In case a single progeny of one mother animal is used as a source, either the entire progeny may be used for compiling the animal population or selected animals of the progeny may be used. Compiling as used herein is carried out with respect to the age of the animals, i.e. all individuals of the population shall have essentially the same age as described below in detail. However, further characteristics may be taken into account. In addition, such as weight, size, sex, overall appearance (e.g. only healthy animal by appearance may be selected). Being of essentially the same age means that the animals have a comparable status of development, e.g. the animals may be embryos, juveniles or adults. A preferred age of the animals to be used in the method of the present invention is an age of the adolescence stage, preferably young adolescence stage. The animals of the animal population, preferably, have an age at start of the experiments with the range of $X\pm1$ day, wherein X is the envisaged age of the animal population. In other words, a given animal of the population shall be at most one day older or younger than the average age of the animals of the animal population. Most preferably, all animals of the population are of age X. Such animals can be provided by compiling animals which are progeny of one litter, i.e. littermates, or which are compiled from different litters from the same day. In case embryos are to be used, it is to be understood that essentially the same age relates to their developmental stages. The developmental stages of embryos from various species can be determined by techniques well known in the art. They may be calculated, e.g., based on the time point of fertilization. Moreover, individual embryos can be developmentally staged due to known morphological features. Moreover, in case embryos are used, it is further to be understood that the pregnant mothers carrying said embryos shall be kept under the conditions referred to herein. If, e.g., rats or mice are used as animals in the method of the present invention, it is preferred that the animals are of age X±1 day, wherein X is 1-3 months after birth. Most preferably, X is 64 days after birth. For dogs, a preferred age (X) shall be 6 month. Keeping as used in accordance with the method of the present invention, refers to particular housing, feeding, drinking and environmental conditions which are applied to the animals of the animal population. It is preferred that the animals are kept under conditions as set forth in the OECD Guideline for the Testing of Chemicals No: 407. Moreover, particular conditions are described as follows.

i) All animals of the animal population are kept under the same constant temperature. Care should be taken to choose a temperature for carrying out the method of the present invention which does not stress the animals. Preferably, temperature should be 20-24±3° C., more preferably 22±3° C., most preferably 22, 23 or 24° C.
  ii) Moreover, all animals of the animal population are kept under the same constant humidity. The humidity should be at least 30%, but should not exceed 70%. However, in rare exceptional situations (such as during room or cage clearing) humidity may even exceed 70%. Preferably, humidity is 50-60%.
  iii) Physical separation of the animals of the animal population has been found to be also important for the method of the present invention. Accordingly, each animal of the animal population must be kept in a separate space, e.g. a separate cage.
  iv) The animals of the animal population are fed ad libitum. The food to be used must be essentially free of chemical or microbial contaminants. The standards to be applied are laid down in Fed. Reg. Vol. 44, No. 91, May 9, 1979, p. 27354. Most preferably, microbial contaminants such as bacteria are below $5 \times 10^5$ cells per g of food. Such food may be purchased from Provimi Kliba SA, Switzerland, as Ground Kliba mouse/rat maintenance diet "GLP" meal.
  v) The animals of the animal population are supplied ad libitum with a drinking liquid. Preferably, said liquid is water. However, other liquids on water basis may be used as well. Such liquids may comprise, for instance, nutritions, vitamins or minerals which are required by the animals. If water is used as drinking liquid, the water shall be free of chemical and microbial contaminants as laid down in the European Drinking Water Directive 98/83/EG.
  vi) Finally, each animal of the animal population must be subjected to the same constant illumination periods. Constant illumination is achieved, preferably, by artificial lightning (having the solar colour spectrum). The illumination period is 12 hours light followed by 12 hours darkness. Then the illumination period starts again. A preferred illumination period, thus, is 12 hours light, e.g. from 6:00 to 18:00, and 12 hours darkness, e.g. from 18:00 to 6:00.

The aforementioned housing conditions can be applied to the animals by using a common storage space for the cages comprising the physically separated animals. Said common storage space may be an animal room or house. By keeping all animals of the population in the same room, constant humidity, temperature and illumination period can be easily achieved by regulating these parameters for the entire room or house. Regulation of the parameters is preferably assisted by automation and the parameters are constantly monitored. Under a first time period sufficient for acclimatization it is to be understood that the animals of the animal population must be kept under the aforementioned particular housing conditions for a time period which allows synchronization of the metabolic activities of the animals so that the animals are acclimatized and have essentially the same metabolome. Specifically, the said first time period shall be of sufficient length as to allow all individuals of the population to adopt the same circadian rhythm, food digestion rhythm, or quiescence/movement periods. Moreover, the first time period shall allow each animal to adjust its biochemical and physiological parameters in response to the applied environmental conditions, such as humidity and temperature. Preferably, said first time period has a length of 5 to 10 days, more preferably 6 to 8, and most preferably 7 days.

Also, the present invention pertains to a data collection comprising characteristic values for the metabolite deoxycytidine or its analytes cytosine and/or ribal.

More preferably, the data collection comprises characteristic values for at least one adrenal corticosteroide as specified elsewhere herein.

The term "data collection" refers to a collection of data which may be physically and/or logically grouped together. Accordingly, the data collection may be implemented in a single data storage medium or in physically separated data storage media being operatively linked to each other. Preferably, the data collection is implemented by means of a database. Thus, a database as used herein comprises the data collection on a suitable storage medium. Moreover, the database, preferably, further comprises a database management system. The database management system is, preferably, a network-based, hierarchical or object-oriented database management system. Furthermore, the database may be a federal or integrated database. More preferably, the database will be implemented as a distributed (federal) system, e.g. as a Client-Server-System. More preferably, the database is structured as to allow a search algorithm to compare a test data set with the data sets comprised by the data collection. Specifically, by using such an algorithm, the database can be searched for similar or identical data sets being indicative for hemolytic anemia or a predisposition thereof (e.g. a query search). Thus, if an identical or similar data set can be identified in the data collection, the test data set will be associated with hemolytic anemia or a predisposition therefor. Consequently, the information obtained from the data collection can be used to diagnose hemolytic anemia or a predisposition therefore based on a test data set obtained from a subject.

Also envisaged by the present invention is a data storage medium comprising the aforementioned data collection of the present invention.

The term "data storage medium" as used herein encompasses data storage media which are based on single physical entities such as a CD, a CD-ROM, a hard disk, optical storage media, or a diskette. Moreover, the term further includes data storage media consisting of physically separated entities which are operatively linked to each other in a manner as to provide the aforementioned data collection, preferably, in a suitable way for a query search.

The present invention further relates to a system comprising
(a) means for comparing characteristic values of metabolites of a sample operatively linked to
(b) a data storage medium as defined above.

The term "system" as used herein relates to different means which are operatively linked to each other. Said means may be implemented in a single device or may be implemented in physically separated devices which are operatively linked to each other. The means for comparing characteristic values of metabolites operate, preferably, based on an algorithm for comparison as mentioned before. The data storage medium, preferably, comprises the aforementioned data collection or database, wherein each of the stored data sets being indicative for hemolytic anemia or a predisposition therefor. Thus, the system of the present invention allows identifying whether a test data set is comprised by the data collection stored in the data storage medium. Consequently, the system of the present invention may be applied as a diagnostic means in diagnosing hemolytic anemia or a predisposition therefor.

In a preferred embodiment of the system, means for determining characteristic values of metabolites of a sample are comprised.

The term "means for determining characteristic values of metabolites" preferably relates to the aforementioned devices for the determination of metabolites such as mass spectrometry devices, NMR devices or devices for carrying out chemical or biological assays for the metabolites.

The present invention encompasses also a diagnostic composition comprising deoxycytidine or its analytes cytosine and/or ribal or means for the determination thereof.

In a preferred embodiment of the said diagnostic composition, the said composition further comprises at least one adrenal corticosteroide as specified elsewhere in this description.

Furthermore, encompassed by the present invention is a diagnostic device comprising
(a) means for determining characteristic values of deoxycytidine or its analytes cytosine and/or ribal; and
(b) means for diagnosing hemolytic anemia or a predisposition therefor based on the characteristic values determined by the means of (a).

More preferably, the device further comprises means for determining characteristic values of at least one adrenal corticosteroide as specified elsewhere herein.

The term "diagnostic means", preferably, relates to a diagnostic device, system or biological or chemical assay as specified elsewhere in the description in detail.

The expression "means for determining characteristic values" refers to devices or agents which are capable of specifically recognizing the metabolite(s). Suitable devices may be spectrometric devices such as mass spectrometry, NMR devices or devices for carrying out chemical or biological assays for the metabolites. Suitable agents may be compounds which specifically detect the metabolites. Detection as used herein may be a two-step process, i.e. the compound may first bind specifically to the metabolite to be detected and subsequently generate a detectable signal, e.g., fluorescent signals, chemiluminescent signals, radioactive signals and the like. For the generation of the detectable signal, further compounds may be required which are all comprised by the term "means for determining characteristic values of a group of metabolites". Compounds which specifically bind to the metabolite are described elsewhere in the specification in detail and include, preferably, enzymes, antibodies, ligands, receptors or other biological molecules or chemicals which specifically bind to the metabolites.

Finally, the present invention pertains to the use of deoxycytidine or its analytes cytosine and/or ribal or means for the determination thereof for the manufacture of a diagnostic device or composition for diagnosing hemolytic anemia in a subject.

In a preferred embodiment of the said use, at least one adrenal corticosteroide as specified elsewhere herein is used in addition to deoxycytidineor its analytes cytosine and/or ribal.

All references referred to above are herewith incorporated by reference with respect to their entire disclosure content as well as their specific disclosure content explicitly referred to in the above description.

The following Examples are merely for the purposes of illustrating the present invention. They shall not be construed, whatsoever, to limit the scope of the invention in any respect.

EXAMPLE

Biomarkers for Aniline-Inducible Hemolytic Anemia

A group of each 5 male and female rats was dosed once daily with aniline at 10 and 100 mg/kg body weight per gavage over 28 days. Additional groups of each 5 male and female animals served as controls. Before starting the treatment period, animals, which were 62-64 days old when supplied, were acclimatized to the housing and environmental conditions for 7 days. All animals of the animal population were kept under the same constant temperature (20-24±3° C.) and the same constant humidity (30-70%). Each animal of the animal population was kept in a separate cage. The animals of the animal population are fed ad libitum. The food to be used was be essentially free of chemical or microbial contaminants. Drinking water was also offered ad libitum. Accordingly, the water was be free of chemical and microbial contaminants as laid down in the European Drinking Water Directive 98/83/EG. The illumination period was 12 hours light followed by 12 hours darkness (12 hours light, from 6:00 to 18:00, and 12 hours darkness, from 18:00 to 6:00).

In the morning of day 7, 14, and 28, blood was taken from the retroorbital venous plexus from fasted anaesthetized animals. From each animal, 1 ml of blood was collected with EDTA as anticoagulant. The samples were be centrifuged for generation of plasma. All plasma samples were covered with a $N_2$ atmosphere and then stored at −80° C. until analysis.

For mass spectrometry-based metabolite profiling analyses plasma samples were extracted and a polar and a non-polar fraction was obtained. For GC-MS analysis, the non-polar fraction was hydrolyzed under acidic conditions to yield the fatty acid methyl esters. Both fractions were further derivatised with a silylating agent before analysis. In LC-MS analysis, both fractions were reconstituted in appropriate solvent mixtures. HPLC was performed by gradient elution on reversed phase separation columns. For mass spectrometric detection metanomics proprietary technology was applied which allows target and high sensitivity MRM (Multiple Reaction Monitoring) profiling in parallel to a full screen analysis. The method resulted in 215 unique analytes for semi-quantitative analysis, about 80 of which are knowns and about 135 of which are unknowns. Moreover, several hundred further analytes giving a fingerprint of the sample are included in the methods.

Following comprehensive analytical validation steps, the data for each analyte were normalized against data from pool samples. These samples were run in parallel through the whole process to account for process variability. The significance of treatment group values specific for sex, dose group and metabolite was determined by comparing means of the treated groups to the means of the respective untreated control groups using Student's t-test. Normalized treatment group values and their significance were fed into a database for further statistics and data mining processes.

The changes of the group of plasma metabolites being indicative for hemolytic anemia after treatment of rats with aniline are shown in the following table:

TABLE 4

Changes of the group of plasma metabolites being indicative for hemolytic anemia observed after treatment of male and female rats for 28 days with aniline at a dose of 100 mg/kg body weight/day by gavage:

| Metabolite | Regulation | Fold change against controls (males/females) | | |
|---|---|---|---|---|
| | | day 7 | day 14 | day 28 |
| 18-hydroxycorticosterone | down | 0.34/0.43 | 0.33*/0.71 | 0.18*/0.47* |
| 11-desoxycortisol | down | 0.47/0.39* | 0.48*/0.71 | 0.27*/0.41* |
| cytosine | up | 1.50*/1.81 | 1.17*/1.18 | 1.71*/1.38 |
| ribal (1,4-anhydro-2-deoxy-D-erythro-pent-1-enitol) (=MetID 407) | up | 1.68/1.79* | 1.42*/1.66* | 1.82*/1.59* |

*statistically significant with $p \leq 0.05$ (Student's t-test)

The invention claimed is:

1. A method for diagnosing hemolytic anemia, comprising:
   (a) determining the amount of at least one of deoxycytidine or its analytes cytosine or ribal in a test sample of a subject suspected to suffer from hemolytic anemia, and
   (b) comparing the amount determined in step (a) to a reference, whereby hemolytic anemia is diagnosed.

2. The method of claim 1, wherein the subject is brought into contact with one or more compounds suspected to be capable of inducing hemolytic anemia.

3. The method of claim 2, wherein the compounds are aromatic amines, oximes or hydroxylamines.

4. The method of claim 1, wherein the reference is derived from (i) a subject which has been brought into contact with aromatic amines, oximes or hydroxylamins, or (ii) a subject which suffers from extravascular hemolytic anemia.

5. The method of claim 4, wherein an identical or similar amount of the at least one of deoxycytidine or its analytes cytosine or ribal in the test sample and the reference is indicative of hemolytic anemia.

6. The method of claim 1, wherein the reference is derived from (i) a subject which has not been brought into contact with aromatic amines, oximes or hydroxylamines, or (ii) a subject known to not suffer from extravascular hemolytic anemia.

7. The method of claim 6, wherein a different amount of the at least one of deoxycytidine or its analytes cytosine or ribal in the test sample in comparison to the reference is indicative of hemolytic anemia.

8. The method of claim 7, wherein an increased amount of the at least one of deoxycytidine or its analytes cytosine or ribal in the test sample in comparison to the reference is indicative of hemolytic anemia.

9. The method of claim 1, wherein the reference is a calculated reference for the at least one of deoxycytidine or its analytes cytosine or ribal for a population of subjects.

10. The method of claim 1, wherein the method further comprises of determining the amount of at least one adrenal corticosteroid in the test sample.

11. The method of claim 10, wherein a decreased amount of the at least one adrenal corticosteroid in the test sample in comparison to the reference is indicative of hemolytic anemia.

12. The method of claim 1, wherein the hemolytic anemia is extravascular hemolytic anemia.

13. The method of claim 12, wherein the extravascular hemolytic anemia is induced by aromatic amines, oximes or hydroxylamines.

14. The method of claim 1, wherein the amount of at least one of deoxycytidine or its analytes cytosine or ribal is determined by mass spectrometry.

15. The method of claim 14, wherein the mass spectrometry is liquid chromatography mass spectrometry (LC-MS) or gas chromatography mass spectrometry (GC-MS).

16. The method of claim 1, wherein the test sample is a sample of a body fluid of said subject.

17. The method of claim 16, wherein the body fluid is blood.

18. The method of claim 1, wherein the subject is a mammal.

19. A method for predicting the likelihood that a subject will develop hemolytic anemia, comprising:
   (a) determining the amount of at least one of deoxycytidine or its analytes cytosine or ribal in a test sample of a subject, and
   (b) comparing the amount determined in step (a) to a reference, whereby the likelihood of said subject to develop hemolytic anemia is predicted.

20. The method of claim 19, wherein the subject is brought into contact with one or more compounds suspected to be capable of inducing hemolytic anemia.

21. The method of claim 20, wherein the compounds are aromatic amines, oximes or hydroxylamines.

22. The method of claim 19, wherein the reference is derived from (i) a subject which has been brought into contact with aromatic amines, oximes or hydroxylamins, or (ii) a subject which suffers from extravascular hemolytic anemia.

23. The method of claim 22, wherein an identical or similar amount of the at least one of deoxycytidine or its analytes cytosine or ribal in the test sample and the reference is indicative of a likelihood that said subject will develop hemolytic anemia.

24. The method of claim 19, wherein the reference is derived from (i) a subject which has not been brought into contact with aromatic amines, oximes or hydroxylamines, or (ii) a subject known to not suffer from extravascular hemolytic anemia.

25. The method of claim 24, wherein a different amount of the at least one of deoxycytidine or its analytes cytosine or ribal in the test sample in comparison to the reference is indicative of a likelihood that said subject will develop hemolytic anemia.

26. The method of claim 25, wherein an increased amount of the at least one of deoxycytidine or its analytes cytosine or ribal in the test sample in comparison to the reference is indicative of a likelihood that said subject will develop hemolytic anemia.

27. The method of claim 19, wherein the reference is a calculated reference for the at least one of deoxycytidine or its analytes cytosine or ribal for a population of subjects.

28. The method of claim 19, wherein the method further comprises determining the amount of at least one adrenal corticosteroid in the test sample.

29. The method of claim 28, wherein a decreased amount of the at least one adrenal corticosteroid in the test sample in comparison to the reference is indicative of a likelihood that said subject will develop hemolytic anemia.

30. The method of claim 19, wherein the hemolytic anemia is extravascular hemolytic anemia or induced by aromatic amines, oximes or hydroxylamines.

31. The method of claim 19, wherein the amount of at least one of deoxycytidine or its analytes cytosine or ribal is determined by mass spectrometry.

32. The method of claim 31, wherein the mass spectrometry is liquid chromatography mass spectrometry (LC-MS) or gas chromatography mass spectrometry (GC-MS).

33. The method of claim 19, wherein the test sample is a sample of a body fluid of said subject.

34. The method of claim 33, wherein the body fluid is blood.

35. A method for diagnosing hemolytic anemia or predicting the likelihood that a subject will develop hemolytic anemia, comprising:
(a) obtaining a test sample from a subject;
(b) pretreating the test sample to obtained a pretreated test sample;
(c) determining the amount of deoxycytidine, or its analytes cytosine and/or ribal, in said pretreated test sample; and
(d) comparing the amount determined in step (c) to a reference,
wherein a difference between the amount of deoxycytidine, or its analytes cytosine and/or ribal, obtained from said pretreated test sample and the reference is indicative that said subject suffers from hemolytic anemia or has a likelihood to develop hemolytic anemia.

36. The method of claim 35, wherein the subject is brought into contact with one or more compounds suspected to be capable of inducing hemolytic anemia.

37. The method of claim 36, wherein the compounds are aromatic amines, oximes or hydroxylamines.

38. The method of claim 35, wherein the reference is derived from (i) a subject which has been brought into contact with aromatic amines, oximes or hydroxylamins, or (ii) a subject which suffers from extravascular hemolytic anemia.

39. The method of claim 38, wherein an identical or similar amount of deoxycytidine, or its analytes cytosine and/or ribal, in the pretreated test sample and the reference is indicative that said subject suffers from hemolytic anemia or has a likelihood to develop hemolytic anemia.

40. The method of claim 35, wherein the reference is derived from (i) a subject which has not been brought into contact with aromatic amines, oximes or hydroxylamines, or (ii) a subject known not to suffer from extravascular hemolytic anemia.

41. The method of claim 35, wherein a different amount of deoxycytidine, or its analytes cytosine and/or ribal, in the pretreated test sample in comparison to the reference is indicative that said subject suffers from hemolytic anemia or has a likelihood to develop hemolytic anemia.

42. The method of claim 41, wherein an increased amount of deoxycytidine, or its analytes cytosine and/or ribal, in the pretreated test sample in comparison to the reference is indicative that said subject suffers from hemolytic anemia or has a likelihood to develop hemolytic anemia.

43. The method of claim 35, wherein the reference is a calculated reference for the deoxycytidine, or its analytes cytosine and/or ribal, for a population of subjects.

44. The method of claim 35, further comprising determining the amount of at least one adrenal corticosteroid in the pretreated test sample.

45. The method of claim 44, wherein a decreased amount of the at least one adrenal corticosteroid in the pretreated test sample in comparison to the reference is indicative that said subject suffers from hemolytic anemia or has a likelihood to develop hemolytic anemia.

46. The method of claim 35, wherein the hemolytic anemia is extravascular hemolytic anemia or induced by aromatic amines, oximes or hydroxylamines.

47. The method of claim 35, wherein the amount of deoxycytidine, or its analytes cytosine and/or ribal, is determined by mass spectrometry.

48. The method of claim 47, wherein the mass spectrometry is liquid chromatography mass spectrometry (LC-MS) or gas chromatography mass spectrometry (GC-MS).

49. The method of claim 35, wherein the test sample is a sample of a body fluid of said subject.

50. The method of claim 49, wherein the body fluid is blood.

51. The method of claim 35, wherein the test sample is pretreated to release and/or separate compounds comprised in said test sample and/or to remove excessive material or waste from said test sample.

* * * * *